(12) United States Patent
Packard et al.

(10) Patent No.: US 8,842,806 B2
(45) Date of Patent: Sep. 23, 2014

(54) APPARATUS AND METHOD FOR BREAST IMAGING

(75) Inventors: Nathan J. Packard, Rochester, NY (US); Samuel Richard, Rochester, NY (US); Dong Yang, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 193 days.

(21) Appl. No.: 13/438,079

(22) Filed: Apr. 3, 2012

(65) Prior Publication Data

US 2013/0259193 A1    Oct. 3, 2013

(51) Int. Cl.
*A61B 6/04* (2006.01)

(52) U.S. Cl.
USPC .............................. 378/37; 378/195; 378/196

(58) Field of Classification Search
CPC ...... A61B 6/025; A61B 6/502; A61B 6/0414; A61B 6/0435
USPC ......................... 378/21, 22, 37, 195, 196, 208
See application file for complete search history.

(56) References Cited

U.S. PATENT DOCUMENTS

| | | | |
|---|---|---|---|
| 3,578,971 A * | 5/1971 | Lasky | 378/37 |
| 4,206,763 A * | 6/1980 | Pedersen | 600/445 |
| 4,433,690 A * | 2/1984 | Green et al. | 600/448 |
| 4,541,436 A * | 9/1985 | Hassler et al. | 600/443 |
| 5,386,447 A * | 1/1995 | Siczek | 378/37 |
| 5,426,685 A * | 6/1995 | Pellegrino et al. | 378/87 |
| 5,820,552 A * | 10/1998 | Crosby et al. | 600/407 |
| 6,254,538 B1 * | 7/2001 | Downey et al. | 600/439 |
| 6,987,831 B2 | 1/2006 | Ning | |
| 7,492,858 B2 * | 2/2009 | Partain et al. | 378/37 |
| 8,374,312 B2 * | 2/2013 | Mansfield | 378/65 |
| 8,406,846 B2 * | 3/2013 | Yoshizawa et al. | 600/407 |
| 8,464,378 B2 * | 6/2013 | Kuo et al. | 378/37 |
| 2006/0094950 A1 | 5/2006 | Ning | |
| 2009/0135996 A1 * | 5/2009 | Muller et al. | 378/37 |
| 2010/0080343 A1 | 4/2010 | Kalender et al. | |
| 2010/0322379 A1 * | 12/2010 | Ohi et al. | 378/37 |

FOREIGN PATENT DOCUMENTS

| | | |
|---|---|---|
| DE | 198 12 995 A1 | 10/1999 |
| EP | 0 435 837 | 7/1991 |
| EP | 1 700 568 | 9/2006 |
| EP | 1 864 611 | 12/2007 |

* cited by examiner

*Primary Examiner* — Glen Kao

(57) ABSTRACT

An apparatus for imaging a breast of a patient has a gantry with a radiation source and a sensor, the source and sensor rotatable in an arcuate orbit about a central axis and within a plane of revolution, wherein the arcuate orbit spans more than 180 degrees and less than 360 degrees, and wherein the gantry has a gantry cover that is disposed to be in contact with at least the chest wall of the patient. The gantry cover has a central opening about the central axis for insertion of the breast that is to be imaged and a peripheral cutout portion that defines the end-points of the arcuate orbit and that provides a space for positioning a portion of the patient's anatomy.

17 Claims, 23 Drawing Sheets

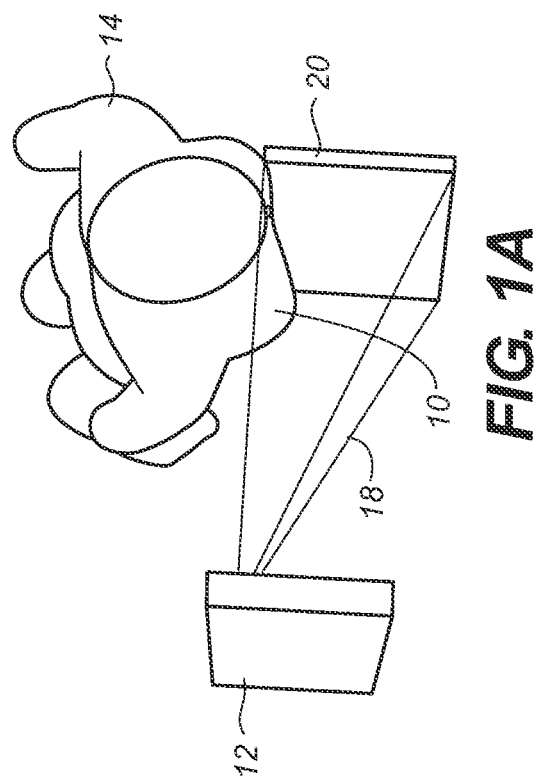

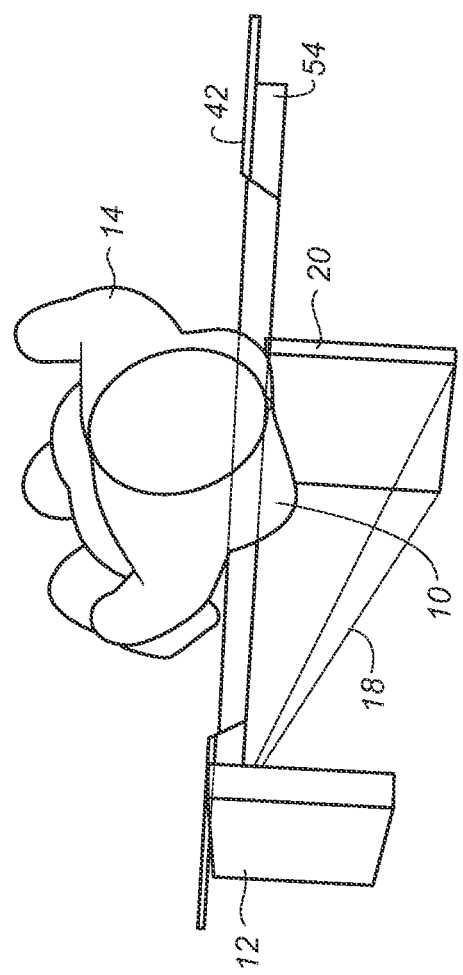

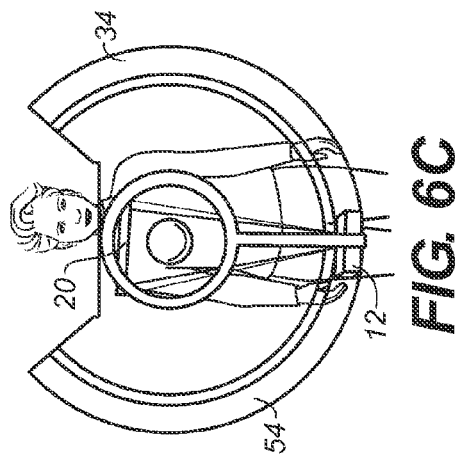
FIG. 6A
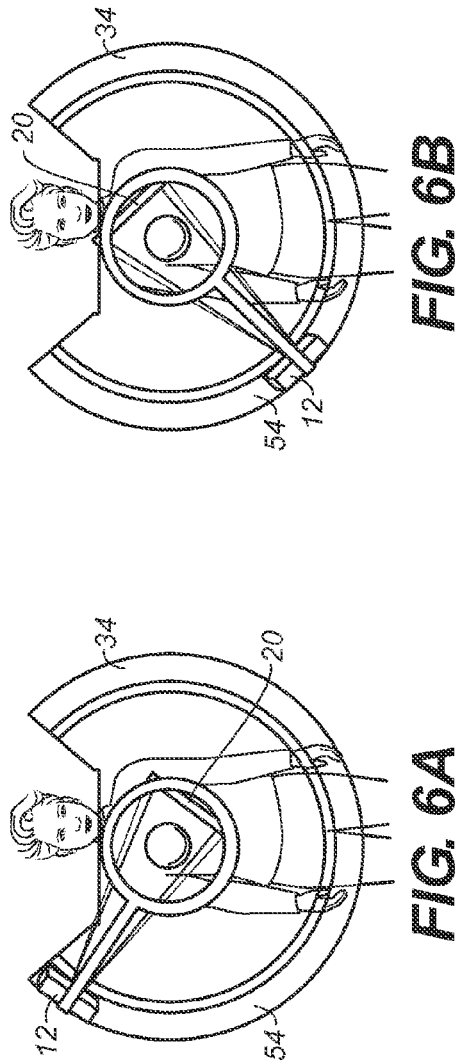
FIG. 6B
FIG. 6C
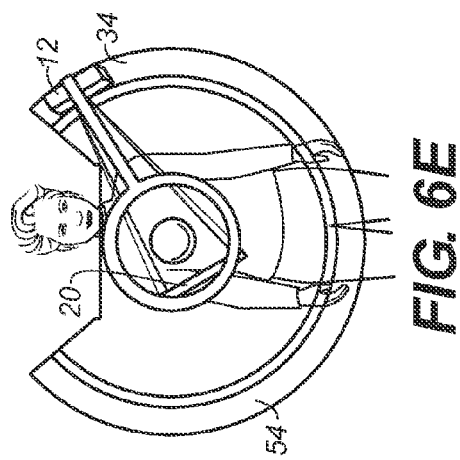
FIG. 6E
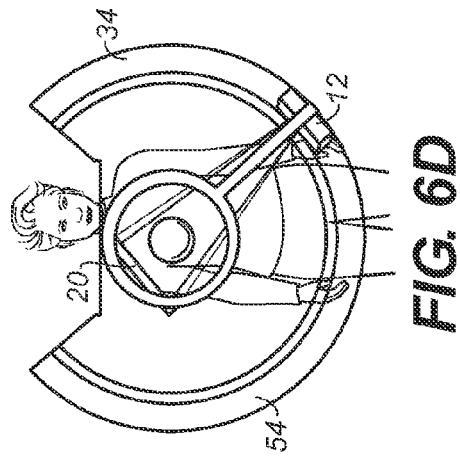
FIG. 6D

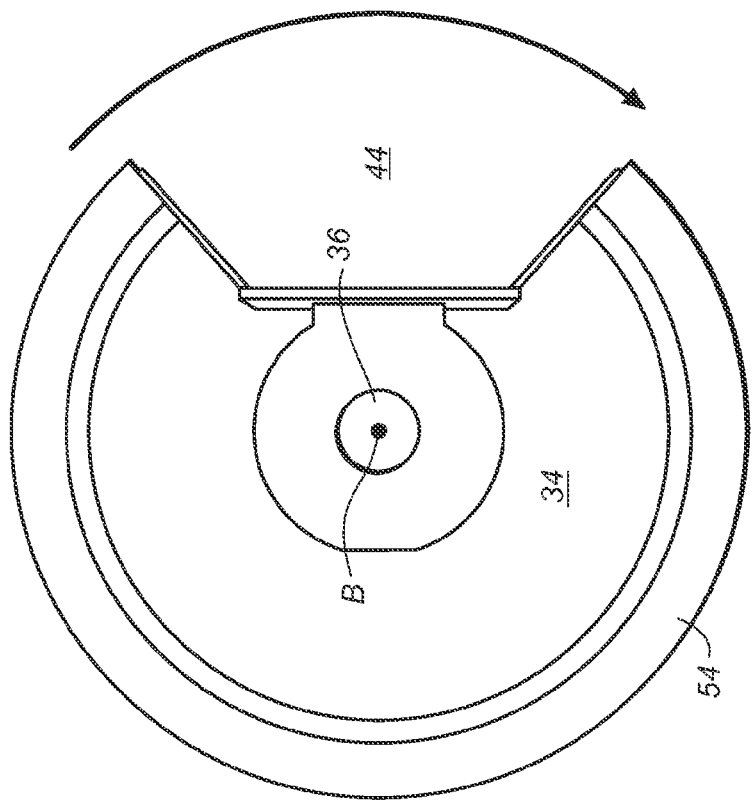
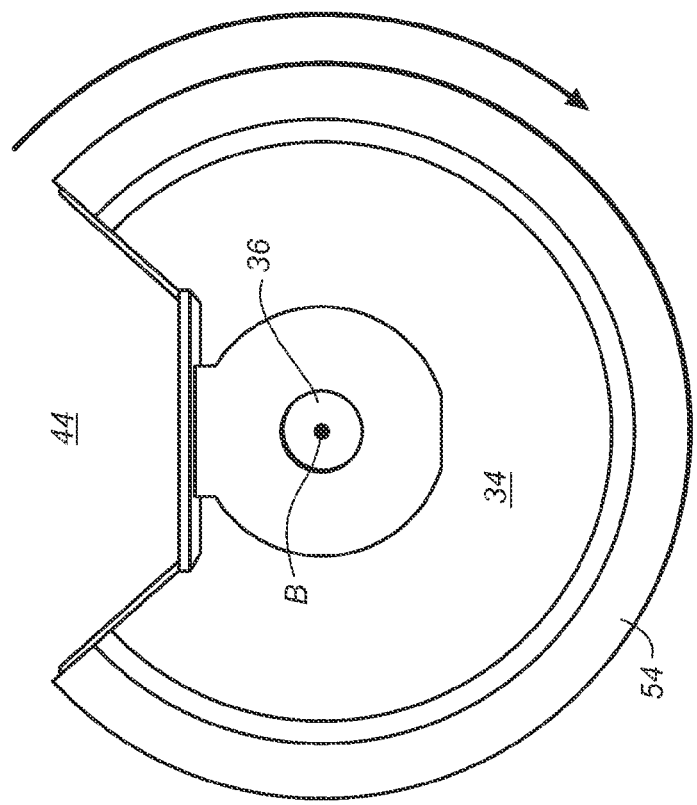

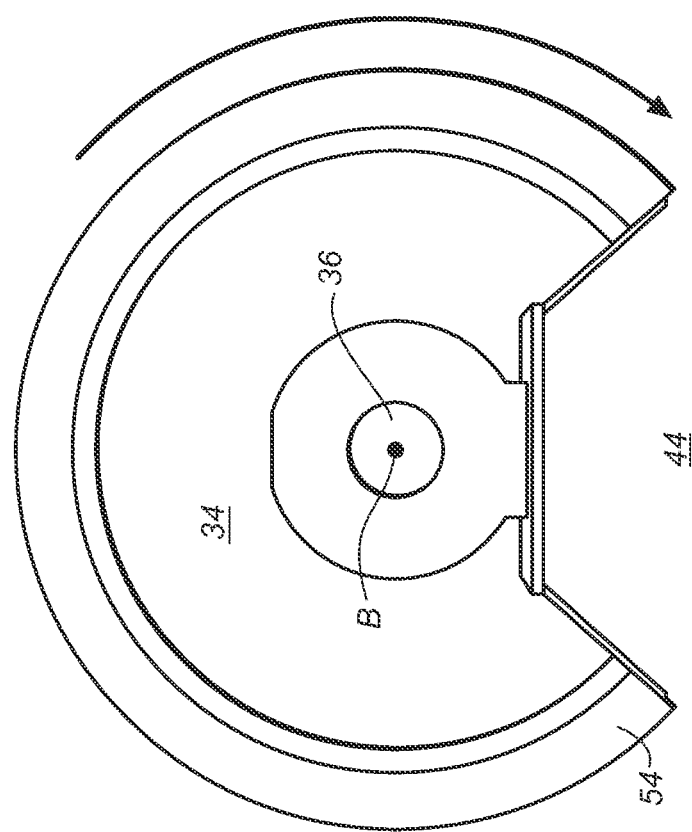

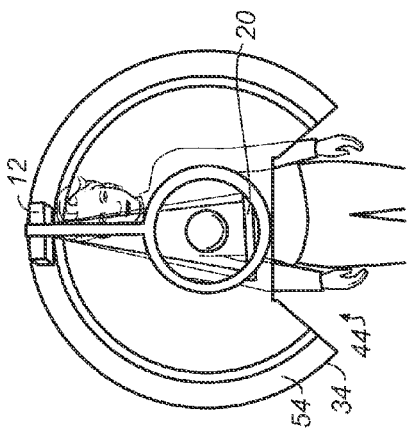
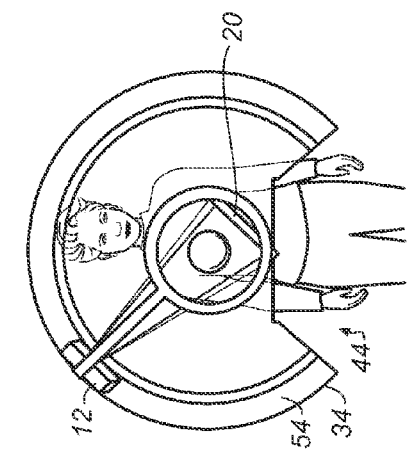
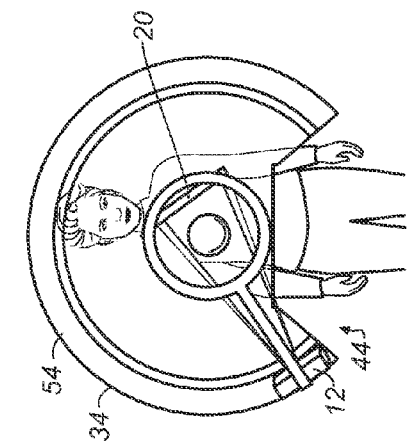
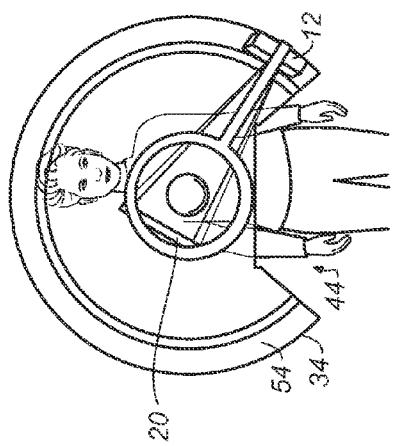
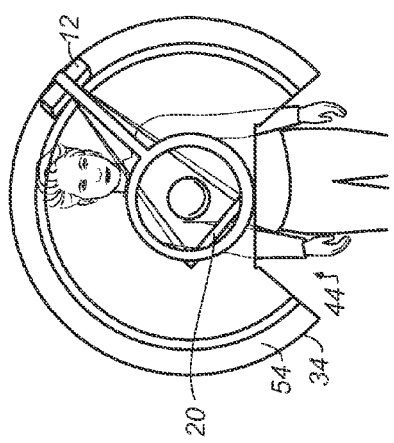

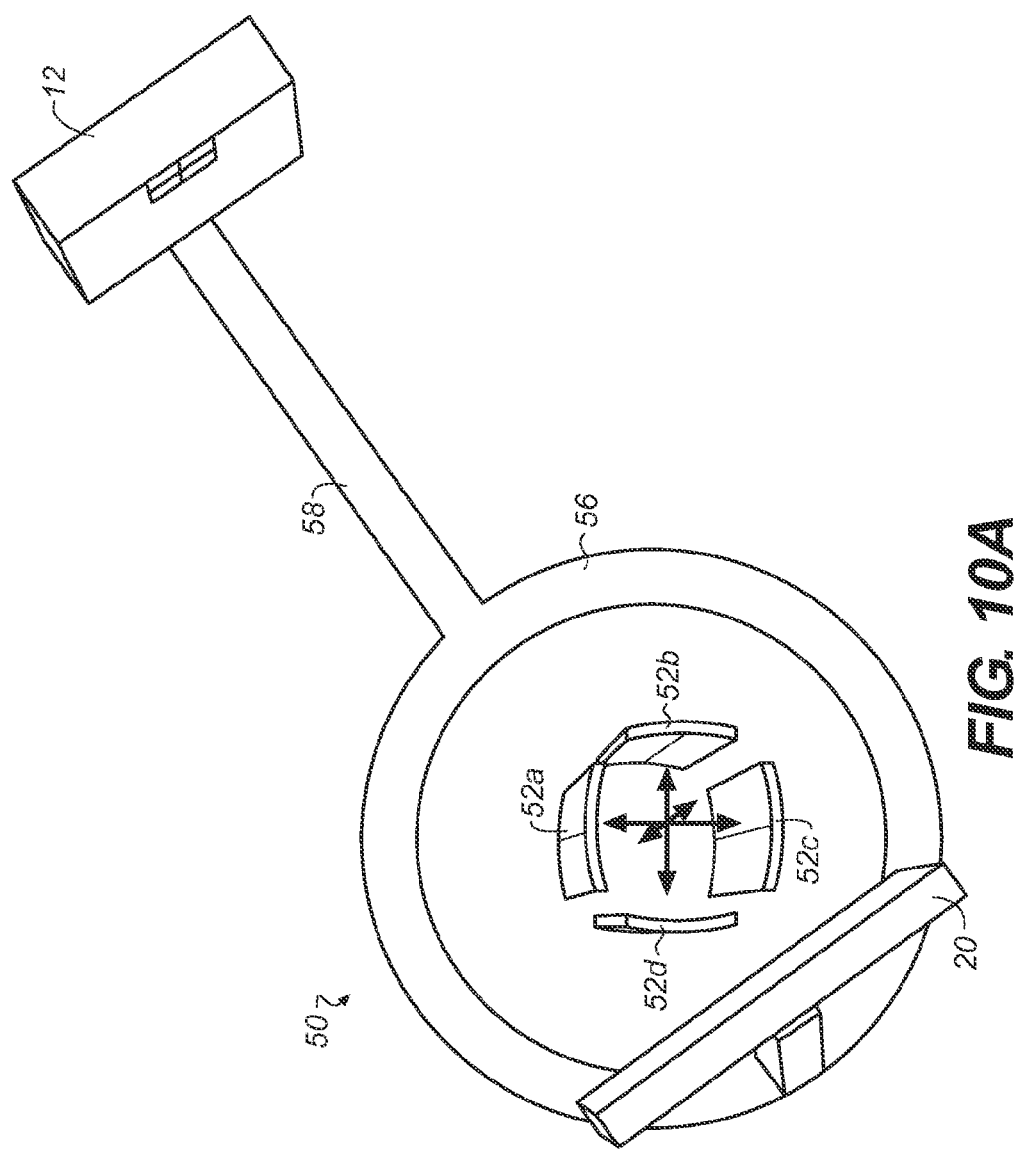

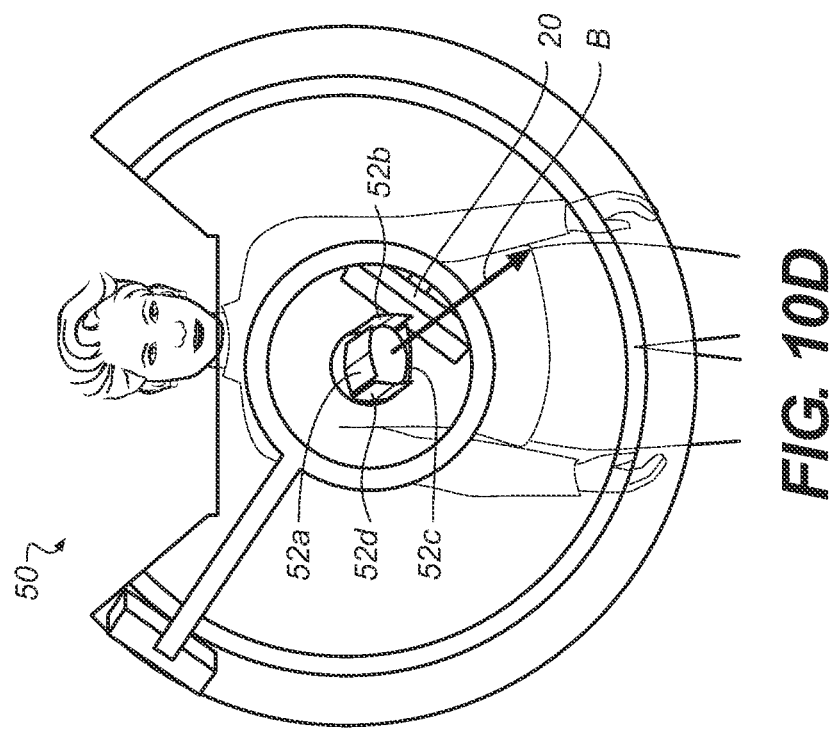

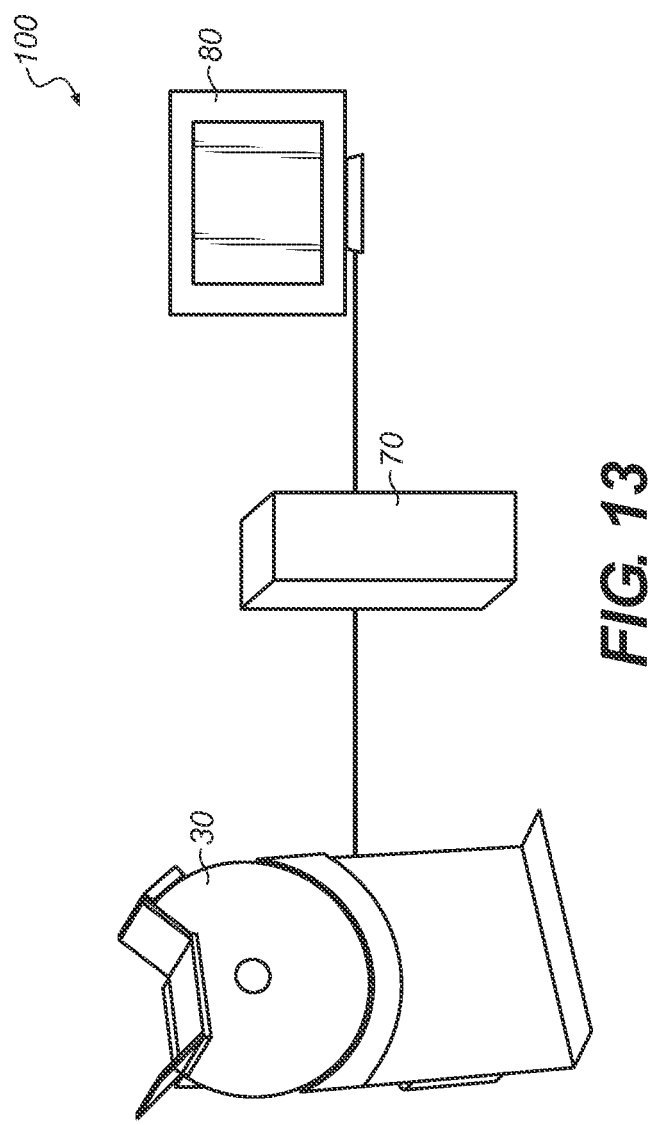

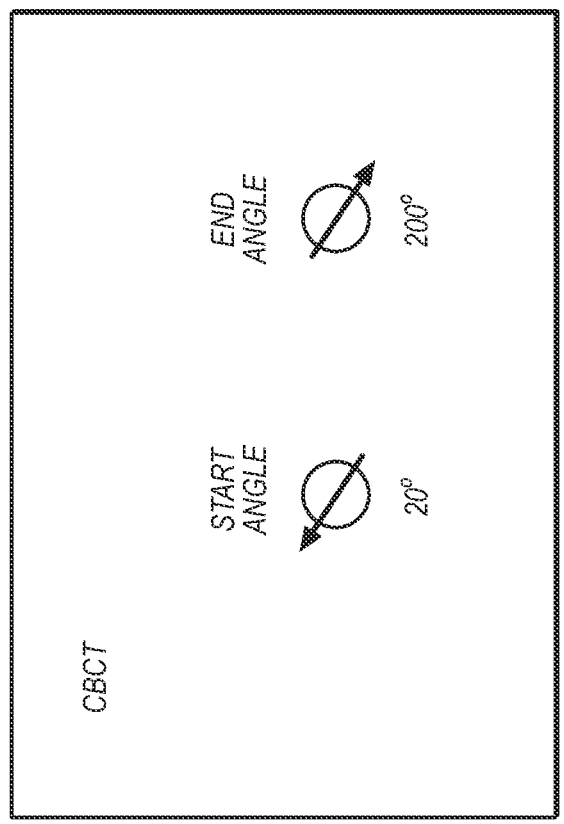

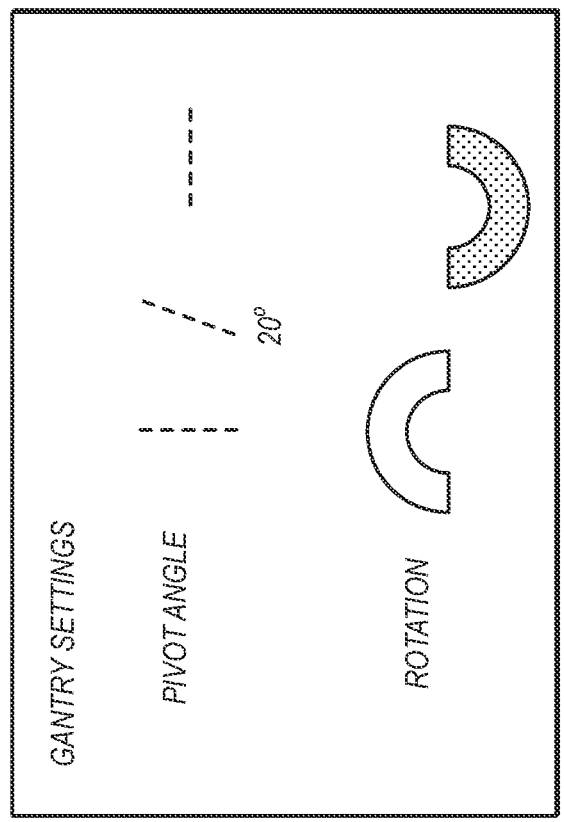

APPARATUS AND METHOD FOR BREAST IMAGING

FIELD OF THE INVENTION

The invention relates generally to the field of medical imaging and more particularly to apparatus and methods for cone beam computed tomography of the breast.

BACKGROUND OF THE INVENTION

Tomographic volume imaging techniques provide enhanced information over conventional two-dimensional mammography and can help to provide data that lead to early diagnosis and treatment of breast cancer. Cone beam computed tomography (CBCT), for example, is acknowledged to have particular advantages for providing volume images that can be suitable for 3-D mammography. The volume images that can be obtained using tomosynthesis, CBCT, and related techniques have the potential to provide information that can be otherwise difficult to ascertain using conventional two-dimensional (2-D) image modalities.

Volume imaging of a subject requires coordinated movement of the radiation source and sensor, with one or both moving over at least a partial revolution about the subject, capturing a succession of two-dimensional (2-D) images at various angular increments. Data from the individual 2-D images is then used to reconstruct a three-dimensional (3-D) or volume image. The angular range within which a subject is scanned, from 0 to a full 360 degrees, affects the amount of 3-D information that can be reconstructed in a volume image. At the one extreme, an angular range of 0 degrees simply corresponds to a standard 2D projection image with no 3-D information. At the other extreme, an angular range of the full 360 degrees corresponds to a typical CBCT exam with complete 3-D information. Tomosynthesis is typically done at angular ranges that are less than 90 degrees and that allow for 3-D reconstruction with some amount of volume information, sometimes termed "quasi-3-D image reconstruction". To reconstruct volume images with full 3-D detail, an angular range of at least 180 degrees plus the fan angle of the radiation source used in the system is required.

For breast imaging, the task of acquiring multiple projections from different angles is complicated by the human anatomy itself, which makes it difficult to position the patient in order to obtain the desired field of view for each of the succession of images that are needed. Optimal imaging conditions would be obtained, for example, by positioning the breast so that the orbit of the source and sensor offers the best possible field of view over all angles being imaged. Attempts to achieve this goal, however, are constrained because of the relative anatomical position of the breast and the limits within which the breast tissue can be extended without considerable patient discomfort.

Proposed solutions for maximizing field of view in breast volume imaging tend to compromise either angular range or patient comfort to achieve this goal. A number of system solutions, for example, take two tomosynthesis scans (cranio-caudal CC and medio-lateral oblique MLO), each within a limited angular range of around ±15 degrees, to provide quasi 3-D information for each scan. Other solutions acquire one scan over a 360 degree range for a full 3-D reconstruction and require the patient to be in a prone position, with the breast pendant through an orifice, using gravity to maximize breast extension into the object field of the volume imaging apparatus. For such a system, however, the patient may be required to bend her back or neck in an awkward and potentially painful attitude during the imaging session. Still other solutions propose using suction or other means to pull forward, into the imaging area, as much of the breast tissue as possible. Such solutions can also lead to patient discomfort.

A workable volume imaging apparatus for 3-D mammography would address each of the following objectives: (i) maintain sufficient field of view to increase, by as much as possible, the amount of breast tissue that can be imaged; (ii) allow comfortable patient positioning, so that the head and neck can be naturally supported during imaging; (iii) allow readily adjustable mechanisms for accommodating the patient, with suitable technician access and features for proper breast positioning and variable extension into the imaging area as needed; and (iv) provide a range of imaging modalities, such as conventional mammography imaging, tomosynthesis, and full 3-D imaging such as CBCT or wide angle tomosynthesis with an angle >=180 degrees plus the fan angle from a single system.

Conventional solutions for volume imaging of the breast have fallen short of some of these objectives and typically compromise one or more of imaging quality, patient comfort, field of view, range of modalities, cost, and ease of adjustment.

SUMMARY OF THE INVENTION

An object of the present invention is to advance the art of 3-D breast imaging and provide a volume imaging apparatus that allows improved patient comfort over conventional systems.

Another object of the present invention is to provide different types of 2-D and 3-D images from a single set of imaging equipment. Embodiments of the present invention flexibly enable different types of imaging, with the patient vertical or at a prone position of a suitable angle.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided an apparatus for imaging a breast of a patient, the apparatus comprising: a gantry comprising a radiation source and a sensor, the source and sensor rotatable in an arcuate orbit about a central axis and within a plane of revolution, wherein the arcuate orbit spans more than 180 degrees and less than 360 degrees, and wherein the gantry has a gantry cover that is disposed to be in contact with at least the chest wall of the patient and wherein the gantry cover has: (i) a central opening about the central axis for insertion of the breast that is to be imaged; and (ii) a peripheral cutout portion that defines the end-points of the arcuate orbit and that provides a space for positioning a portion of the patient's anatomy.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 1A is a schematic diagram showing the cone of radiation directed toward the breast.

FIG. 1B is a schematic diagram showing the cone of radiation directed toward the breast, with a protective cover to support and shield the patient.

FIGS. 6A through 6E are plan views that show portions of the sequence for CBCT imaging, with the gantry cover in position for a standing patient.

FIGS. 7A, 7B, and 7C show different rotational positions of the gantry cover of the breast imaging apparatus.

FIGS. 8A through 8E are plan views that show portions of the sequence for CBCT imaging, with the gantry cover in position for a seated patient or for imaging over an alternate range of angles relative to the patient.

FIG. 10A shows parts of an extension apparatus for breast imaging according to an embodiment of the present invention.

FIG. 10D shows compression paddles in an alternate configuration, in which the alternate pair of opposed paddles are used.

FIG. 13 is a schematic view of a breast imaging system according to an embodiment of the present invention.

FIGS. 14A, 14B, 14C, and 14D show exemplary operator interface screens that display on a control console according to an embodiment of the present invention.

DETAILED DESCRIPTION OF THE INVENTION

Figure 2:
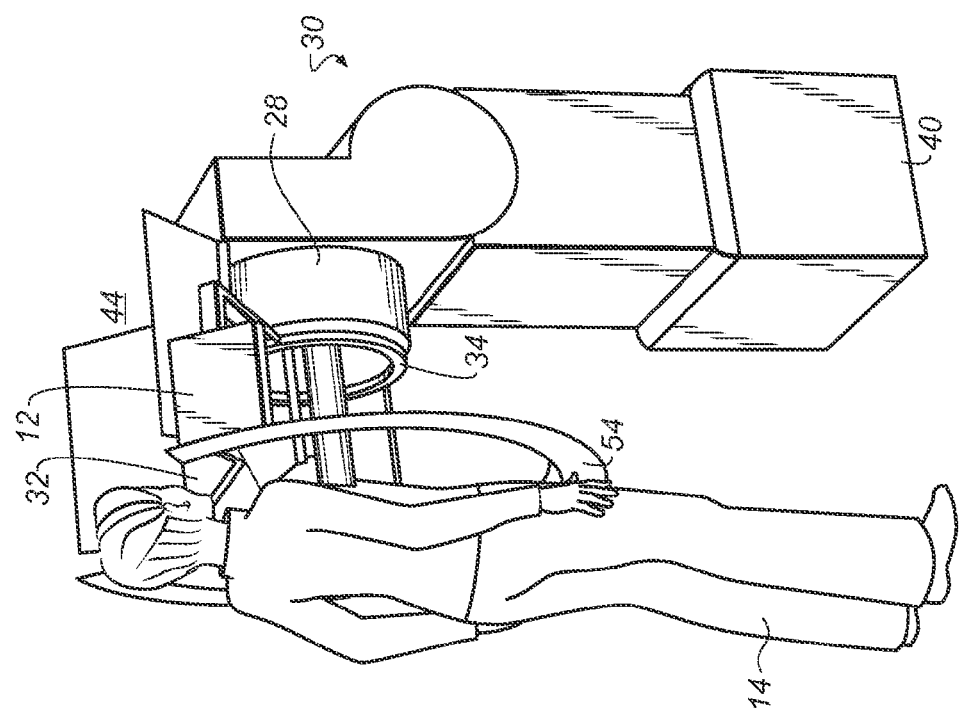
FIG. 2 is a perspective view that shows a breast imaging apparatus according to an embodiment of the present invention.

The following is a detailed description of the preferred embodiments of the invention, reference being made to the drawings in which the same reference numerals identify the same elements of structure in each of the several figures.

Where they are used, the terms "first", "second", "third", and the like, do not necessarily denote any ordinal or priority relation, but are used for more clearly distinguishing one element or time interval from another. For example, there are no fixed "first" or "second" elements in what is described herein; these descriptors are merely used to clearly distinguish one element from another similar element in the context of the present disclosure.

An issue with existing volume imaging solutions for breast imaging, as noted above, relates to the field of view. Referring to FIG. 1A, there is shown a top view of imaging components for imaging a breast 10 of a patient 14. The imaging system provides a radiation source 12 and a sensor 20, such as a digital receiver (DR) or other type of sensor. Radiation source 12 is approximated as a point source providing a cone beam 18. The optimal location of this point source would provide radiation throughout the breast tissue, without appreciable radiation outside this region. To provide the most useful information for diagnosis, the point source needs to be relatively close to the chest wall of the patient, with the breast tissue urged forward into optimal position. In practice, it is difficult to achieve this optimal positioning for all patients, but some approximation is generally achievable.

FIG. 1B shows a top view of the imaging arrangement of FIG. 1A supplemented by the front section 42 of a gantry cover 54 that provides a contact surface, supports the patient, and helps to shield the patient from radiation and from moving parts of the imaging system. The front section 42 of the gantry cover 54 is designed to minimize the distance from the patient to the radiation from cone beam 18.

For volume imaging, the breast is imaged at multiple angles. This requires coordinated movement of source 12 and/or sensor 20 around the breast. In practice, for volume imaging only partial revolution of source 12 and/or sensor 20 about the breast is needed. For cone beam computed tomography (CBCT), for example, the needed orbit is 180 degrees plus the fan angle. The needed orbit for tomosynthesis imaging can be much less, such as +/−20 degrees, for example. Tomosynthesis imaging is typically done from two views (cranio-caudal CC and medio-lateral oblique MLO) as shown in more detail subsequently. The coordinated movement maintains source 12 and sensor 20 at opposing positions orbiting about an axis of revolution, with the breast centered at or near the axis of revolution and the axis of revolution relatively close to the sensor. Two-dimensional (2-D) imaging is available at any angle of revolution.

In practice, the idealized conditions for breast imaging geometry is mediated by patient anatomy itself and by the desire to allow comfortable positioning of the patient. It is advantageous to keep the orbit of the sensor 20 about the breast small in radius, while allowing sufficient distance between the radiation source 12 and the breast. Further concerns relate to the need for a mechanism to gently compress and urge the breast forward into a suitable position for volume imaging. Embodiments of the present invention provide a system allows both 2-D and 3-D imaging in a number of modes, adapted to the ergonomic requirements of patient anatomy.

Figure 3A:
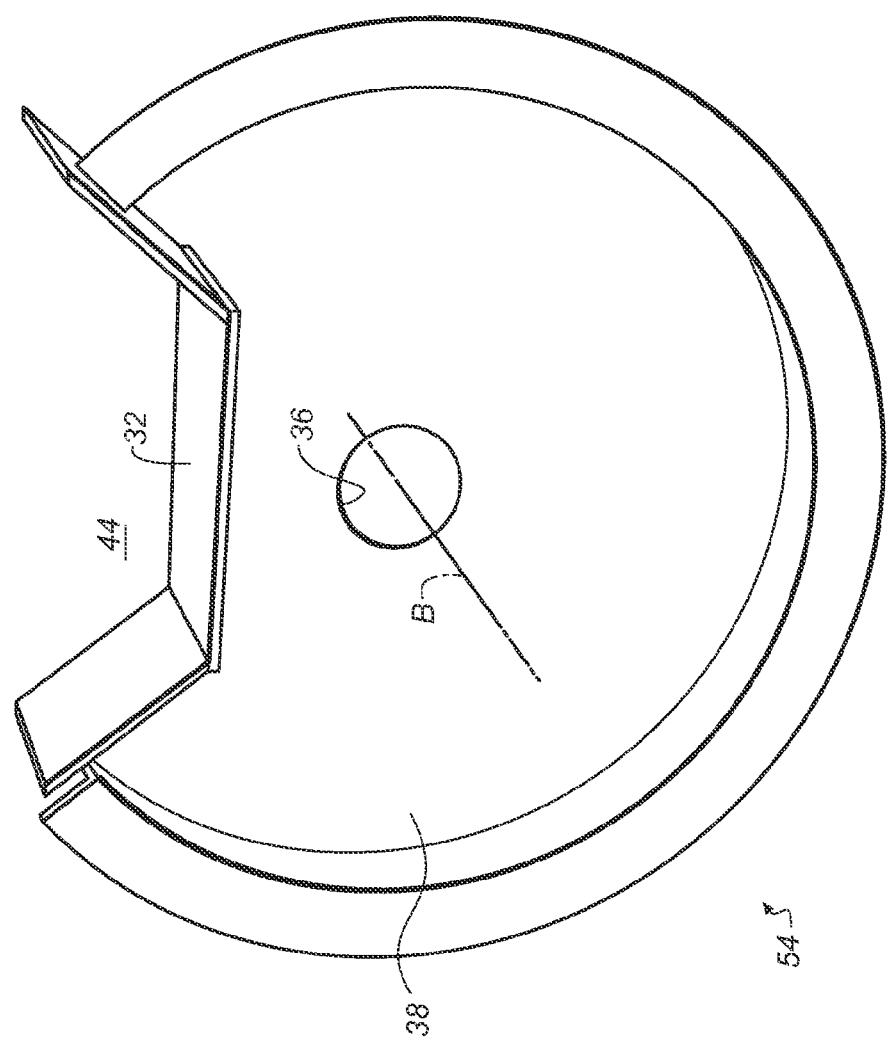
FIG. 3A is a perspective view of the gantry cover used for the breast imaging apparatus of FIG. 2.
Figure 3B:
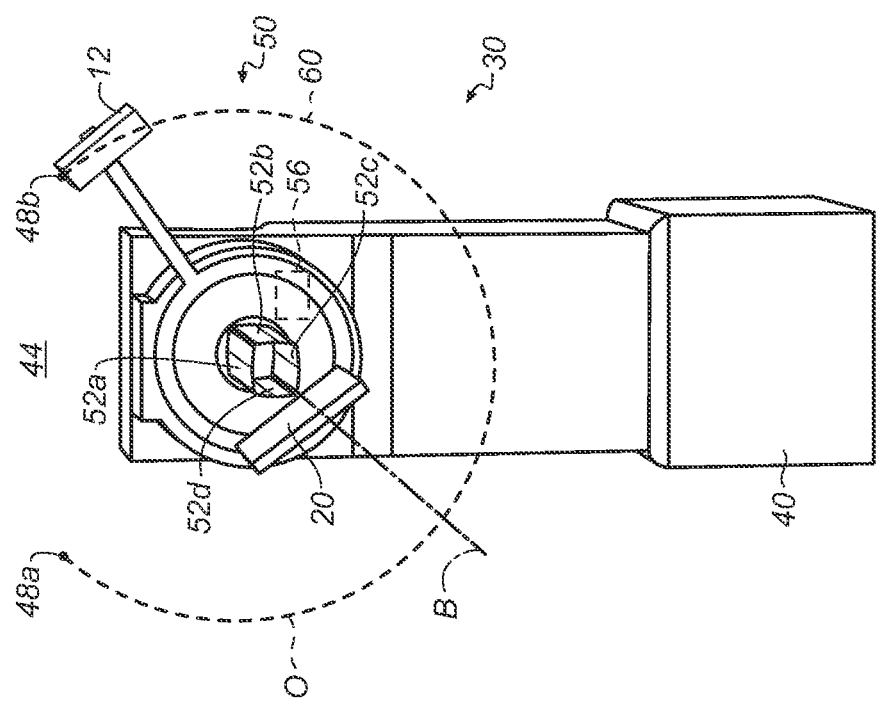
FIG. 3B is a perspective view that shows a breast imaging apparatus with gantry cover and other components removed.

The perspective view of FIG. 2 shows a breast imaging apparatus 30 according to an embodiment of the present invention. FIGS. 3A and 3B show particular components of imaging apparatus 30 that are obstructed in FIG. 2 or removed for better visibility of underlying mechanisms. A patient 14 can stand or be seated in front of imaging apparatus 30, shown standing erect or leaning slightly forward into position in FIG. 2, with comfortable support for the chin provided by an adjustable support 32. The patient 14 does not need to bend her neck or position herself in a less comfortable prone position. Support 32 can include additional shielding from stray radiation.

A covered arcuate gantry 34 has an opening or port 36, about a central axis B, into which the breast is inserted. A cover 54 of gantry 34 is represented as translucent in FIG. 2 for better visibility and is shown separately in FIG. 3A. Cover 54 can be translucent or opaque. Gantry cover 54 has a peripheral cutout portion 44 that constrains rotational motion of gantry 34, which revolves behind gantry cover 54, allowing revolution of source 12 and detector 20 to any number of suitable positions along an arc of at least 180 degrees but less than 360 degrees. Peripheral cutout portion 44 defines endpoints of the allowed orbit for gantry 34 components. Gantry cover 54 itself can be rotated to different positions, repositioning cutout portion 44 to suit different imaging requirements, as shown in more detail subsequently. Cover 54 is featured with an indented portion 38 surrounding opening 36 that allows patient 14 to be positioned forward of imaging components within gantry 34. A support base 40 supports gantry 34 with its cover 54 that covers the internal mechanical components of gantry 34 that move during imaging and protects these components from patient contact and from the environment and can also provide some shielding from radiation.

Gantry 34 and cover 54 can be moved vertically, as a unit, toward or away from base 40 to a comfortable height for the patient. With the patient 14 in the standing position shown, peripheral cutout portion 44 and chin support 32 allow comfortable positioning of the head within the extended orbit of internal source and sensor components within gantry 34. Opening or port 36 is formed about central axis B; preferably axis B is at or near the geometric center of opening or port 36. An actuator 28, such as a motor, provides rotation of gantry 34 components during volume imaging.

The perspective view of FIG. 3B shows imaging apparatus 30 with gantry cover 54 and other components removed for better visibility. Source 12 and detector 20 are movable to revolve synchronously within a plane of orbit 60 about the subject breast within an arc. Extreme end-points 48a and 48b of an arcuate orbit O of gantry 34 are defined by the position of cutout portion 44, as shown. Given the relative position of cutout portion 44, the arcuate orbit that can be traversed by gantry 34 components lies between extreme end-points 48a and 48b. As is described subsequently, the position of cutout portion 44 can be rotated, effectively changing the angular position of the end-points of the arcuate orbit O that is available. Peripheral cutout portion 44 can be rotated to a suitable angle to allow positioning of the patient's head, legs, arm, or other extremity during imaging. The angular position of cutout portion 44 can be sensed using any of a number of types of sensor elements 56 that indicate an angle of inclination or rotation of a shaft, plate, or other device. Types of sensors that can be used include, but would not be limited to, contact sensors, infrared sensors, optical encoders, potentiometers, tilt sensors, capacitive devices, inductive devices, resolvers, and the like. In an alternate embodiment, the angular position of cutout portion 44 is not sensed directly; instead, one or more limit switches are used to indicate end-of-travel positions that correspond to end-points 48a and 48b in FIG. 3B. It should be noted that different sensor elements 56 can be used for internal components that rotate within gantry 34 and for gantry 34 itself.

FIG. 3B also shows an extension apparatus 50 having a set of paddles 52a, 52b, 52c, and 52d disposed to adjustably compress and urge the breast into a suitable position for imaging according to an embodiment of the present invention. Paddles 52a, 52b, 52c, and 52d extend or retract along an axis B and are adjustable to move inward toward or outward away from axis B to suit the breast size.

Figure 4:
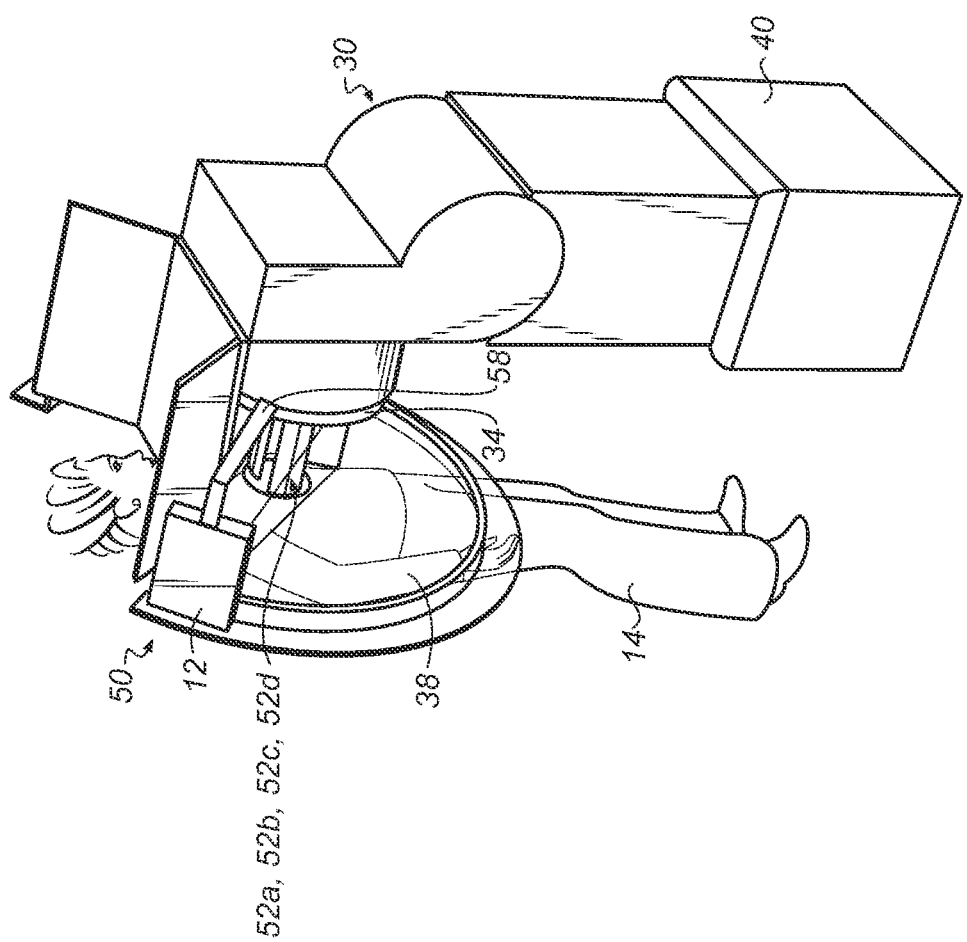
FIG. 4 is a perspective view that shows the imaging apparatus from a rear view.

The perspective view of FIG. 4 shows a view of imaging apparatus 30 from the rear. Source 12 is shown extended on an arm 58 that is coupled to gantry 34 for providing the orbital movement of sensor 20 (not visible in FIG. 4) and source 12. The function of indented portion 38 can be better appreciated from this view, allowing the patient 14 to extend forwardly into the orbit of source 12 and sensor 20.

FIG. 4 also shows how the technician has ready access to the breast positioning mechanism of extension apparatus 50 from the rear of apparatus 30. The technician can view the position of paddles 52a, 52b, 52c, and 52d and make proper adjustments once the patient is leaning forward into position. A hinged access door (not shown) or other access opening can be provided for this purpose.

Figure 5B:
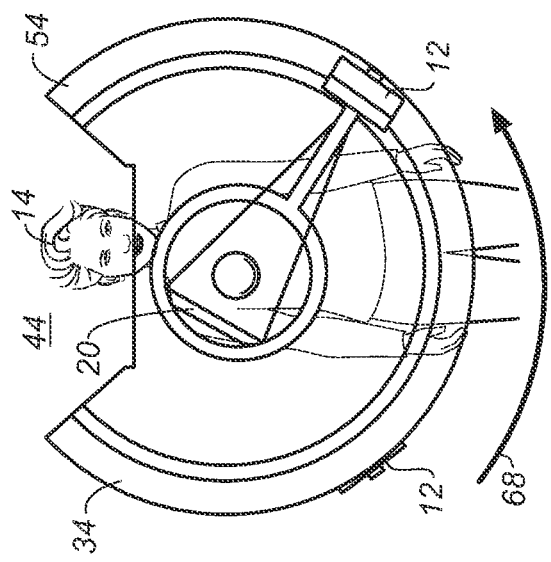
FIG. 5B is a schematic view showing a tomosynthesis imaging sequence for a CC view.
Figure 5A:
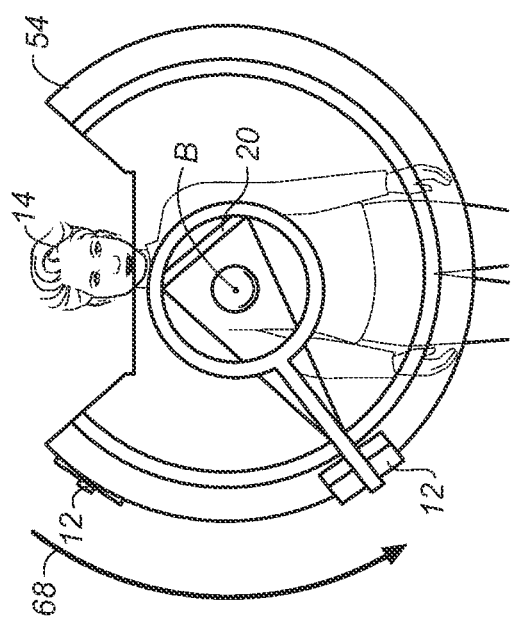
FIG. 5A is a schematic view showing a tomosynthesis imaging sequence for an MLO view.

Among its particular features is the ability of apparatus 30 to obtain images in 2-D and 3-D modalities. The schematic view of FIGS. 5A and 5B show, in plan view form, a tomosynthesis imaging sequence with an angular span 68 that extends over a small arc for medio-lateral (MLO) and caudocranial (CC) views, respectively. Motion is shown as counterclockwise from the view of FIGS. 5A and 5B; revolution can alternately be in the opposite direction. Rotation of source 12 and sensor 20 about a normal axis B, extending out from the page in the view of FIGS. 5A and 5B, can be over an adjustable range of angles, so that angular span 68 can be adjusted by operator settings, for example, with the arc of orbit beginning and ending at any suitable position. Axis B extends within opening 36, preferably at or very near the center of opening 36 (FIG. 3A).

The sequence of schematic views beginning in FIG. 6A and progressing through FIGS. 6B, 6C, 6D, and 6E shows a CBCT imaging sequence over a range of angles that spans 180 degrees plus the fan angle. This range of angles provides sufficient image data for full 3-D volume reconstruction. An image is obtained at each of a number of angular increments, such as at each increment of 1 degree, 1.5 degree, or 2 degrees in the orbital revolution about the breast, for example.

As the schematic diagrams of FIGS. 5A through 6E suggest, 2-D imaging of the breast can be obtained at any angle with corresponding positioning of source 12 and sensor 20. Thus, for example, 2-D imaging to obtain a single breast image at any suitable angle is easily accomplished using imaging apparatus 30. With the arrangement shown, the same imaging apparatus 30 can be used for 2-D imaging, for tomosynthesis imaging over a relatively limited angular range, or for CBCT imaging to provide a full volume image.

Imaging apparatus 30 can rotate gantry cover 54 so that peripheral cutout portion 44 has a suitable angular position to allow room for the head, legs, or other extremities. The sequence of FIGS. 7A, 7B, and 7C shows gantry cover 54 rotated about normal axis B from an initial position, with cutout portion 44 provided at chin level, to an intermediate position, with cutout portion 44 at the side, and finally to a bottom position in FIG. 7C that allows room for the patient's legs. With cutout portion 44 in any position, the arc that is available for imaging extends substantially from one side of cutout portion 44 to the other. According to an embodiment of the present invention, gantry cover 54 rotates independently of internal gantry 34 components, such as source 12 and sensor 20. With this arrangement, control logic for gantry 34 movement senses the angular position of peripheral cutout portion 44 and restricts the arcuate orbit of revolution for internal components to angles defined by this angular position.

Figure 9:
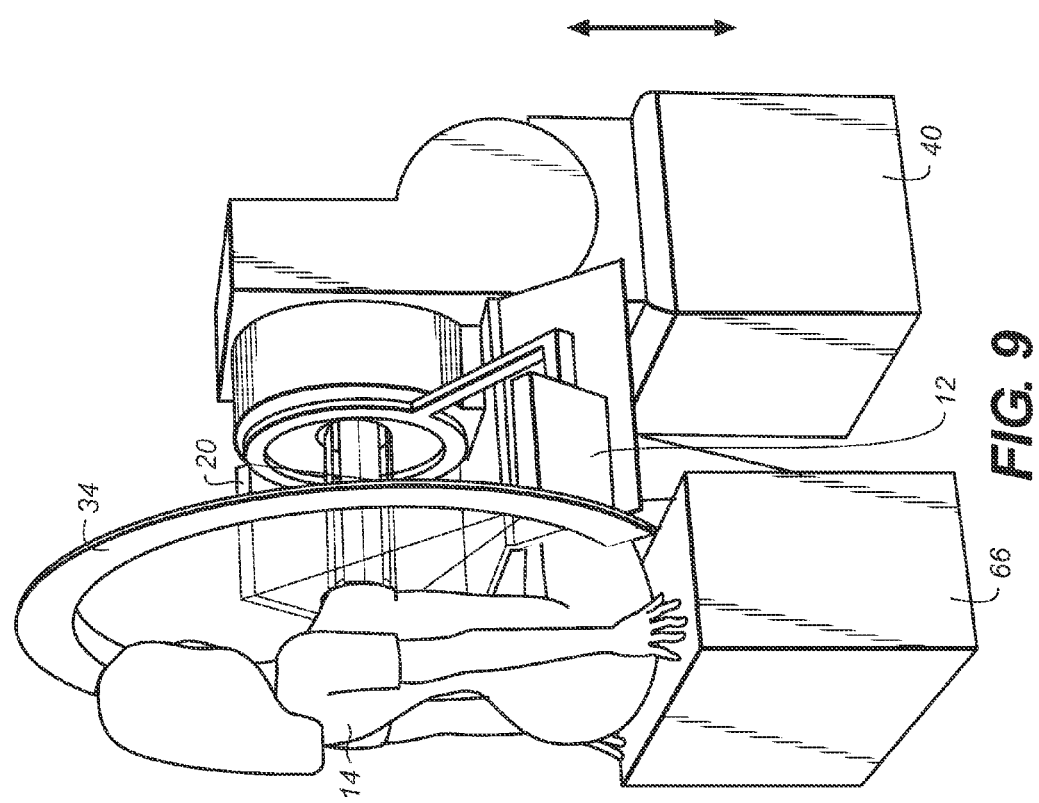
FIG. 9 is a perspective view of the breast imaging apparatus configured for imaging a seated patient.

The sequence of schematic views beginning in FIG. 8A and progressing through FIGS. 8B, 8C, 8D, and 8E shows a CBCT imaging sequence with gantry cover 54 rotated so that cutout portion 44 is at its bottom position, as shown in FIG. 7C. The perspective view of FIG. 9 shows how this feature can be used for patient 14 in a sitting position at imaging apparatus 30. Height adjustment, as shown by the arrow in FIG. 9, enables the vertical height of gantry 34 to be suitably adjusted for the patient, seated on a seat 66.

Comparing the positioning of gantry cover 54 shown in FIGS. 6A-6E with the positioning used for the sequence of FIGS. 8A-8E, it can be seen that imaging apparatus 30 using rotatable gantry cover 54 is capable of directing radiation to the breast from above or below. Thus, for 2-D radiographic imaging, imaging apparatus 30 can obtain a conventional cranial-caudal (CC) image using the position shown in FIG. 8C, for example; alternately, by directing the radiant energy from below as in the position shown in FIG. 6C, a caudo-cranial image can be obtained. Thus, in addition to allowing the selection of a range of angles about the breast for volume imaging, embodiments of the present invention also give the radiologist additional flexibility for selecting a desired view angle for 2-D imaging.

Figure 10C:
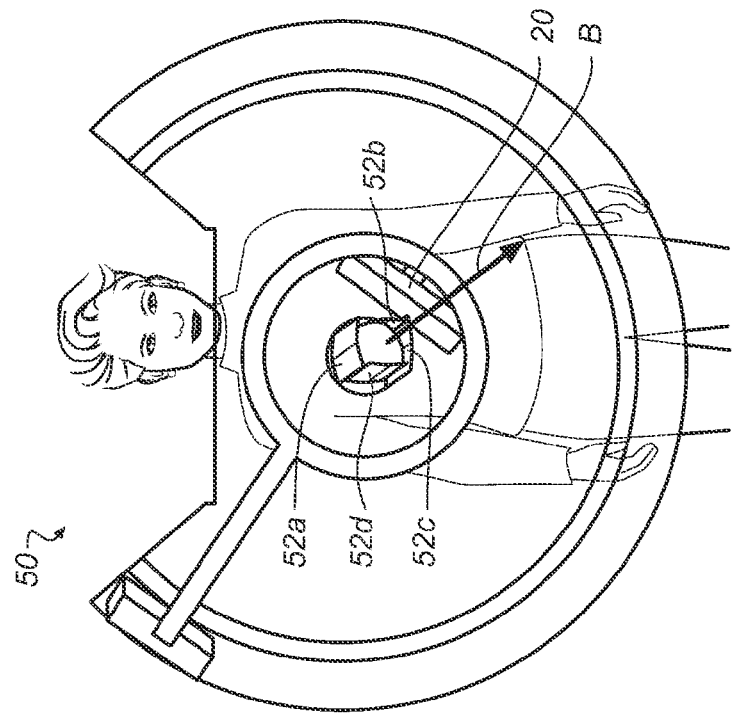
FIG. 10C shows compression paddles in a second configuration, in which one pair of opposed paddles are used.
Figure 10B:
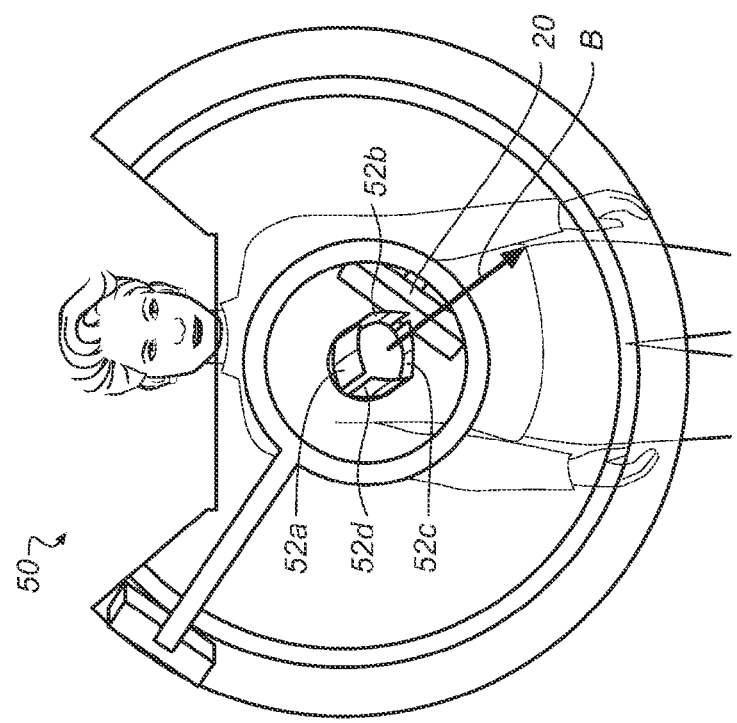
FIG. 10B shows compression paddles in a first configuration, in which two pairs of opposed paddles are used.

As noted, imaging apparatus 30 can employ a four-paddle extension apparatus 50. The perspective view of FIG. 10A shows an arrangement of paddles 52a, 52b, 52c, and 52d, paired so that paddle 52a is opposite paddle 52c and these paddles operate in a first direction; similarly paddle 52b is opposite paddle 52d and these paddles operate in a second direction that is orthogonal to the first direction. Both pairs of paddles can be used, or either pair separately, in any combination. According to an alternate embodiment of the present invention, extension apparatus 50 can be rotated about axis B, so that paddles can be horizontal, vertical, or at any other appropriate angle, with paired paddles maintained at 180 degrees from each other. FIGS. 10B, 10C, and 10D show different positions of paddles 52a, 52b, 52c, and 52d. In FIG. 10B, all four paddles are used to compress the patient's breast. In FIG. 10C, one pair of paddles, shown as paddles 52b and 52d are used. In FIG. 10D, the alternate pair of paddles 52a and 52c are used to compress the breast. Paddles 52a, 52b, 52c, and 52d can be individually extended or retracted and separately angled relative to axis B, both along axis B and skewed with respect to axis B, to accommodate different patient anatomy and imaging angles. Paddles 52a, 52b, 52c, and 52d can be manually positioned or adjusted automatically by the technician.

Figure 11A:
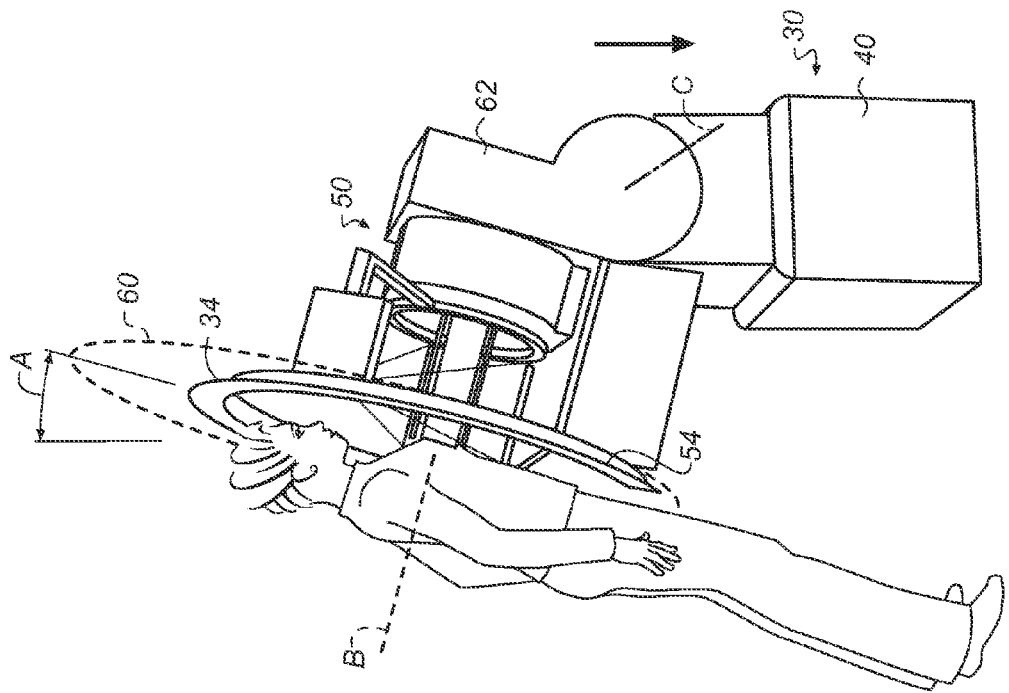
FIG. 11A is a side view of the imaging apparatus with the gantry and cover in a vertical orientation.
Figure 11B:
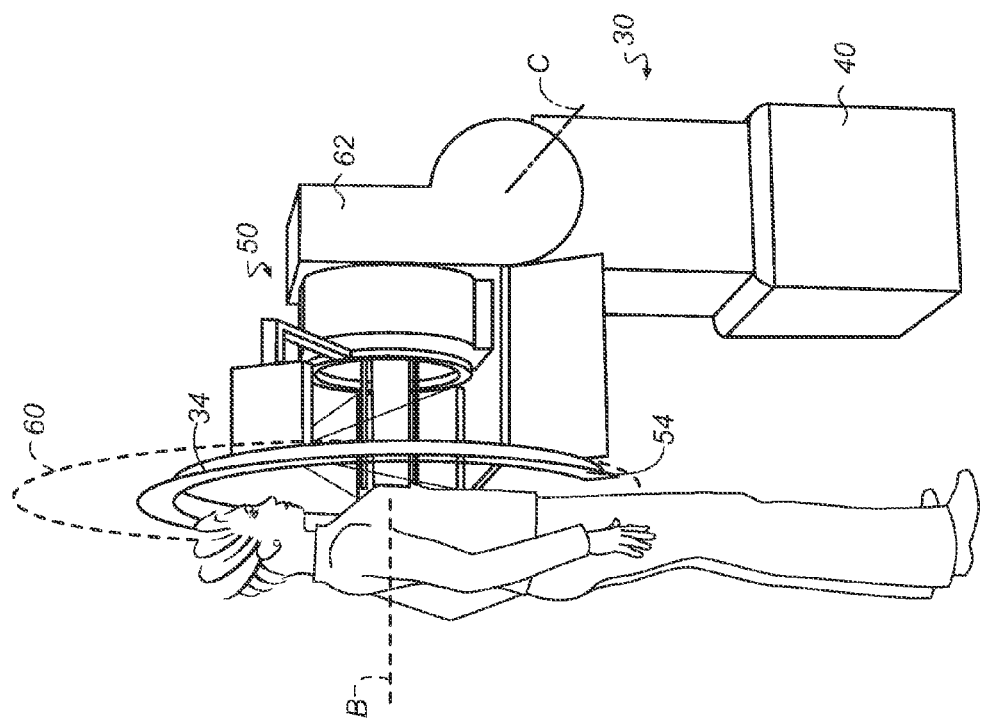
FIG. 11B is a side view of the imaging apparatus with the gantry and cover pivoted at an angle.

FIGS. 11A and 11B show how gantry 34 and cover 54 can be pivoted to change an inclination angle A. This changes the inclination of the plane of orbit 60, allowing patient 14 to be in a partially prone position. This effectively changes the inclination of axis B, as shown. In this embodiment, a pivoting member 62 pivots at least a few degrees about an axis C. In addition, a height adjustment is also provided to lower gantry 34 and cover 54, as indicated by the arrow in FIG. 11B.

Figure 12B:
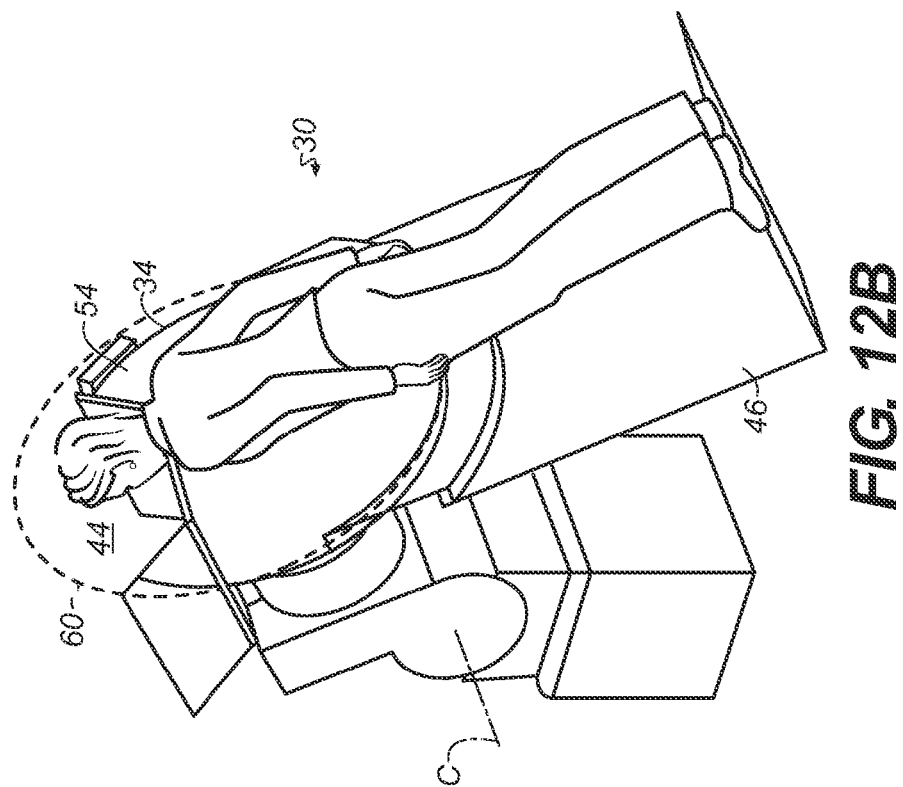
FIGS. 12A, 12B, and 12C show an embodiment of the imaging apparatus with a support table pivoted to various positions.
Figure 12A:
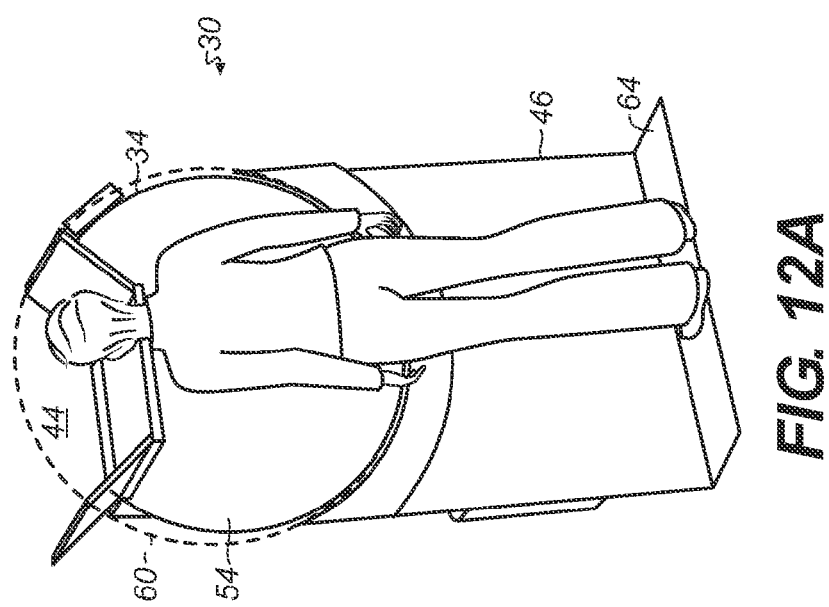
Figure 12C:
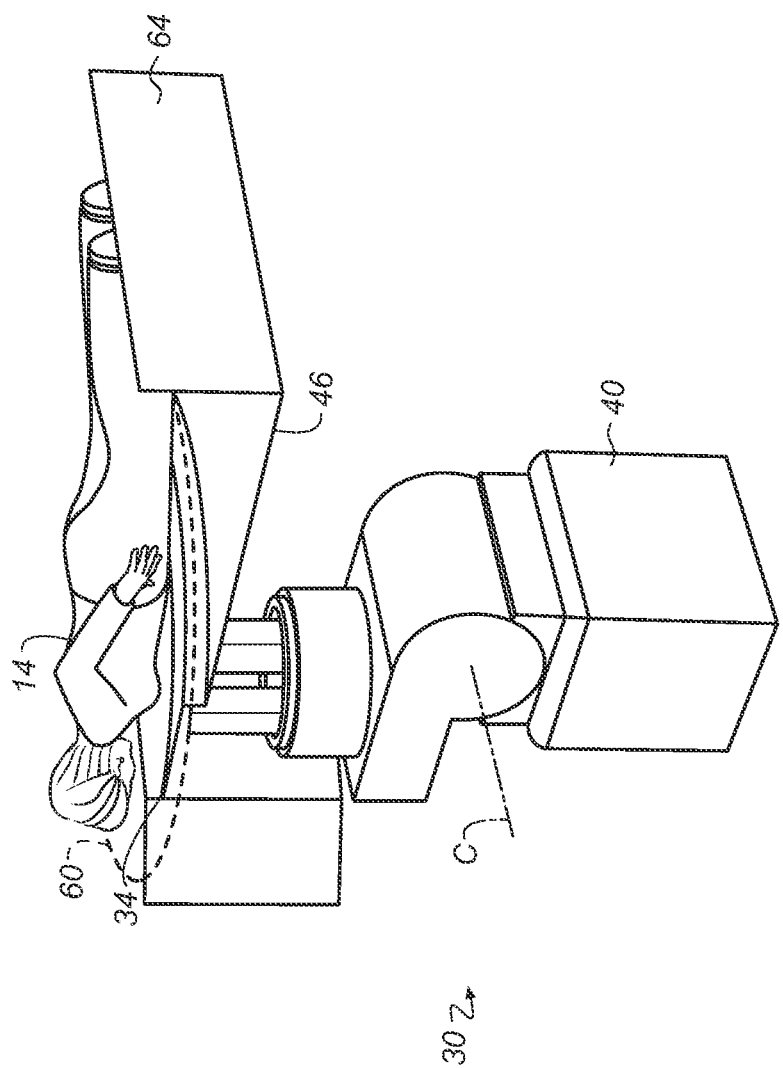

FIGS. 12A, 12B, and 12C show the use of a pivoting support table 46, which is coupled to gantry cover 54 or is an extension of gantry cover 54, that enables rotation of patient 14 to a fully prone position, as shown in FIG. 12C. Using table 46, the plane of orbit 60 can be changed in suitable increments from 0 to 90 degrees relative to horizontal, for example. The patient stands on a standing ledge 64. This arrangement allows the patient to be set up in the more comfortable standing position, then rotated into the prone position if desired. This prone position has advantages for allowing the patient to undergo additional diagnostics or treatment procedures such as breast biopsy, tumor ablation, or radiation therapy while lying on the same platform as is used for mammography screening.

FIG. 13 is a schematic view of a breast imaging system 100 according to an embodiment of the present invention. Imaging apparatus 30 is in signal communication with a control logic processor 70 for transfer of control, status, and data. A control console 80 provides an operator interface for setup of breast imaging system 100 in various modes.

Figure 14A:
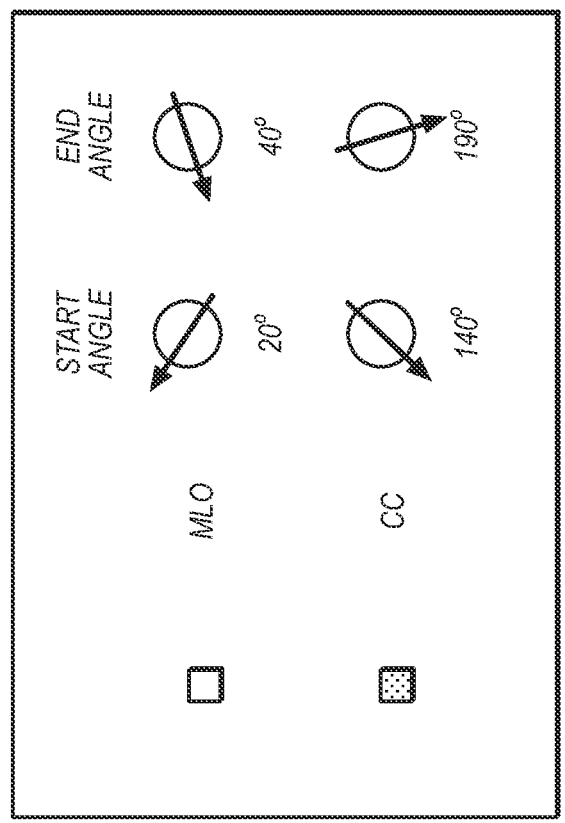

FIGS. 14A, 14B, 14C, and 14D show exemplary operator interface screens that display on control console 80 according to an embodiment of the present invention. Additional screens (not shown) would allow operator entry of standard technique settings, such as kVp and other settings, for example. FIG. 14A shows a control screen 82 that allows the operator to specify operation in one or both tomosynthesis modes or for 2-D mode, whether for MLO or CC imaging. Symbols can be manipulated to indicate start and ending angles for the scan. For 2-D imaging, the start and ending angles would be the same, for example. Operator instructions entered on this interface screen are then provided to imaging apparatus 30 to control internal operation of gantry 34 components.

Figure 14C:
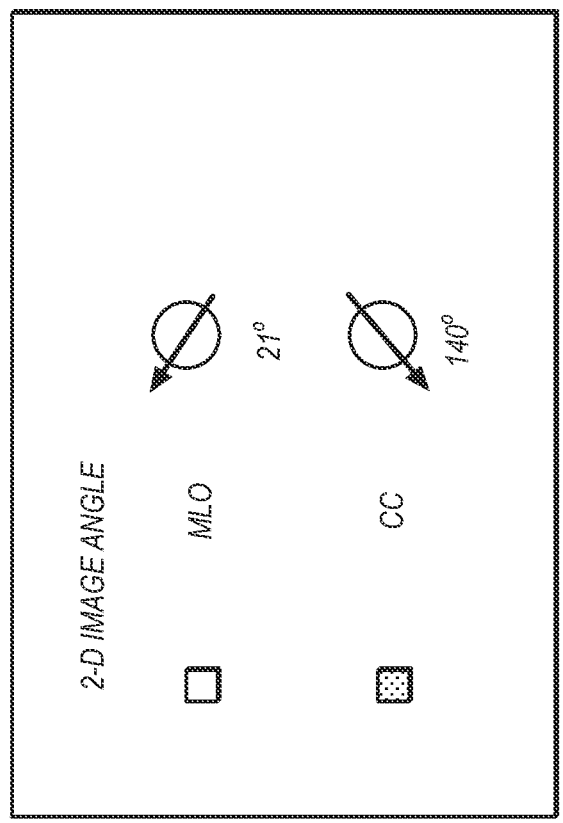

In similar manner, FIG. 14B shows a CBCT interface control screen 84. The operator can enter commands that specify start and end angle, as well as angular increments or other suitable data. FIG. 14C shows an operator interface control screen 90 for setting the angle for a 2-D MLO or CC image. FIG. 14D shows operator entry of various settings for gantry 34 positions, such as pivot angle and rotation, as shown, on a control screen 86. According to an embodiment of the present invention, this gantry setup data is stored with the image data. The gantry settings can be controlled using this screen, operating motors (not shown) that control the angle of gantry cover 54 and position of cutout portion 44 accordingly. In an alternate embodiment, sensors coupled with gantry cover 54 are used to identify the rotation angle of the gantry and the location of the cutout portion 44. Starting and ending angles of rotation can also be stored with the image data.

It can be appreciated that the imaging apparatus configuration of embodiments of the present invention is readily adaptable to accommodate differences in patient height, size, and other anatomy differences. The patient does not need to assume an uncomfortable position and is able to rest her chin against a support without uncomfortable bending of the neck or spine. The patient is able to bend at the waist to accommodate a more prone position or a sitting position. In the prone position, the patient is able to avoid uncomfortable bending of the neck or spine.

The apparatus of the present invention is capable of obtaining volume images of CBCT or tomosynthesis types, over angular ranges set by the operator, either using an operator interface, or by manual adjustment of gantry 34 components. The apparatus of the present invention is capable of obtaining 2-D images from any angle that is within the possible range of movement of gantry 34.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. An apparatus for imaging a breast of a patient, comprising:
   a gantry comprising an x-ray radiation source and a sensor, the x-ray radiation source and sensor being rotatable in an arcuate orbit about a central axis and within a plane of revolution, wherein the arcuate orbit spans more than 180 degrees and less than 360 degrees, and wherein the gantry has a gantry cover that is disposed to be in contact with at least the chest wall of the patient and wherein the gantry cover includes:
      a central opening about the central axis for insertion of the breast that is to be imaged; and
      a peripheral cutout portion that defines the end-points of the arcuate orbit and that provides a space for positioning a portion of the patient's anatomy.

2. The apparatus of claim 1 wherein a portion of the gantry cover that surrounds the central opening is indented.

3. The apparatus of claim 1 further comprising an extension apparatus within the gantry, the extension apparatus comprising a plurality of paddles for support and extension of the patient's breast within the central opening.

4. The apparatus of claim 1 further comprising an extension apparatus for the breast, the apparatus comprising first and second opposed pairs of paddles, wherein the first pair of paddles is adjustable with respect to a first direction and the second pair of paddles is adjustable with respect to a second direction that is orthogonal to the first direction.

5. The apparatus of claim 1 wherein the gantry is coupled to a base and wherein the height of the gantry with respect to the base is adjustable.

6. The apparatus of claim 1 wherein the gantry is pivotable for inclining the plane of revolution and adjusting the inclination of the patient.

7. The apparatus of claim 1 wherein the gantry cover is rotatable independently from rotation of the x-ray radiation source and sensor about the central axis.

8. The apparatus of claim 1 further comprising a support table that is coupled to the gantry cover and that is pivotable along with the gantry for supporting the patient at an angle of inclination.

9. The apparatus of claim 8 wherein the support table includes a standing ledge for the patient.

10. The apparatus of claim 1 wherein an angular span of the orbit is adjustable by an operator.

11. An apparatus for imaging a breast of a patient, comprising:
a gantry mounted on a base comprising an x-ray radiation source and a sensor, the x-ray radiation source and sensor rotatable in an arcuate orbit about a central axis and within a plane of revolution that has an inclination angle, wherein the arcuate orbit spans more than 180 degrees and less than 360 degrees, and wherein the gantry has a gantry cover that is disposed to be in contact with at least the chest wall of the patient and wherein the gantry cover is rotatable independently from gantry rotation and includes:
(i) a central opening about the central axis for insertion of the breast that is to be imaged; and
(ii) a peripheral cutout portion that defines the endpoints of the arcuate orbit and that provides a space for positioning a portion of the patient's anatomy;
wherein the gantry is pivotable on the base to adjust the inclination angle of the plane of revolution.

12. The apparatus of claim 11 wherein a portion of the gantry cover that surrounds the central opening is indented.

13. The apparatus of claim 11 further comprising an extension apparatus within the gantry, the extension apparatus comprising a plurality of paddles for support and extension of the patient's breast within the central opening.

14. The apparatus of claim 11 wherein the gantry is coupled to a base and wherein the height of the gantry with respect to the base is adjustable.

15. The apparatus of claim 11 further comprising a support table that is coupled to the gantry cover and that is pivotable along with the gantry for supporting the patient at an angle of inclination.

16. The apparatus of claim 11 wherein an angular span of the orbit is adjustable by an operator.

17. A method for imaging a breast of a patient, comprising:
providing a covered gantry comprising an x-ray radiation source and a sensor, the x-ray radiation source and sensor rotatable in an arcuate orbit about a central axis and within a plane of revolution, wherein the arcuate orbit spans more than 180 degrees and less than 360 degrees, and wherein the gantry has a gantry cover that is disposed to be in contact with at least the chest wall of the patient and wherein the gantry cover includes:
(i) a central opening about the central axis for insertion of the breast that is to be imaged; and
(ii) a peripheral cutout portion that defines the endpoints of the arcuate orbit and that provides a space for positioning a portion of the patient's anatomy;
sensing rotation of the gantry cover to an angular position for positioning the patient;
accepting instructions that identifies at least a first angle for a scan over a range of angles;
obtaining a plurality of images of the patient over the range of angles; and
displaying, transmitting, or storing at least one of: the first angle, a second angle, and the sensed angular position of gantry rotation.

* * * * *